United States Patent
Neumann

(10) Patent No.: US 12,340,893 B2
(45) Date of Patent: Jun. 24, 2025

(54) SYSTEM AND METHOD FOR GENERATING A GESTATIONAL DISORDER NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

(*) Notice: Subject to any disclaimer, the term of this patent is extended or adjusted under 35 U.S.C. 154(b) by 0 days.

(21) Appl. No.: 18/522,039

(22) Filed: Nov. 28, 2023

(65) Prior Publication Data
US 2024/0105308 A1    Mar. 28, 2024

Related U.S. Application Data

(63) Continuation of application No. 17/187,983, filed on Mar. 1, 2021, now Pat. No. 11,854,685.

(51) Int. Cl.
*G16H 20/60*     (2018.01)
*C12Q 1/6883*    (2018.01)
*G16H 50/20*     (2018.01)

(52) U.S. Cl.
CPC .......... *G16H 20/60* (2018.01); *C12Q 1/6883* (2013.01); *C12Q 2600/156* (2013.01); *G16H 50/20* (2018.01)

(58) Field of Classification Search
CPC ............ C12Q 2600/156; C12Q 1/6883; G16H 50/20; G16H 20/60
See application file for complete search history.

(56) References Cited

U.S. PATENT DOCUMENTS

| | | |
|---|---|---|
| 7,074,183 B2 | 7/2006 | Castellanos |
| 7,970,620 B2 | 6/2011 | Brown |
| 8,226,414 B2 | 7/2012 | Bodin |

(Continued)

FOREIGN PATENT DOCUMENTS

| | | |
|---|---|---|
| RU | 2691145 C2 | 6/2019 |
| WO | 2014015378 | 1/2014 |

(Continued)

OTHER PUBLICATIONS

Zerfu and Ayele Nutrition Journal 2013, 12:20. http://www.nutritionj.com/content/12/1/20 (Year: 2013).*

(Continued)

*Primary Examiner* — Christopher L Gilligan
*Assistant Examiner* — Tristan Isaac Evans
(74) *Attorney, Agent, or Firm* — Caldwell Intellectual Property Law

(57) ABSTRACT

A system for generating a gestational disorder nourishment program comprising a computing device, the computing device configured to obtain a maternal marker, calculate a gestational phase as a function of the maternal marker, wherein calculating the gestational phase further comprises, identifying a gestational goal, and calculating the gestational phase as a function of the maternal marker and the gestational goal as a function of a gestational machine-learning model, determine an edible as a function of the gestational phase, and generate a nourishment program as a function of the edible.

18 Claims, 7 Drawing Sheets

(56) References Cited

U.S. PATENT DOCUMENTS

| | | | |
|---|---|---|---|
| 8,560,336 | B2 | 10/2013 | Schwarzberg |
| 8,684,922 | B2 | 4/2014 | Tran |
| 10,373,522 | B2 | 8/2019 | Byron |
| 2002/0046060 | A1* | 4/2002 | Hoskyns ............... G16H 10/20 705/2 |
| 2006/0074279 | A1 | 4/2006 | Evgeny |
| 2006/0199155 | A1 | 9/2006 | Mosher |
| 2010/0042438 | A1 | 2/2010 | Moore |
| 2010/0070455 | A1 | 3/2010 | Halperin |
| 2010/0136508 | A1 | 6/2010 | Zekhtser |
| 2013/0261183 | A1 | 10/2013 | Bhagat |
| 2014/0345234 | A1* | 11/2014 | Thierman .......... A61K 36/9068 426/648 |
| 2015/0161355 | A1 | 6/2015 | Karra |
| 2015/0356885 | A1 | 12/2015 | Chen |
| 2016/0225284 | A1 | 8/2016 | Schoen |
| 2018/0308389 | A1 | 10/2018 | Moser |
| 2019/0074080 | A1 | 3/2019 | Appelbaum |
| 2019/0221303 | A1 | 7/2019 | Bennett |
| 2019/0251861 | A1 | 8/2019 | Wolf |
| 2020/0138362 | A1* | 5/2020 | Koumpan ............... A61B 5/486 |
| 2024/0186001 | A1* | 6/2024 | Martignetti ...... G01N 33/57442 |

FOREIGN PATENT DOCUMENTS

| | | |
|---|---|---|
| WO | 2019054737 | 3/2019 |
| WO | 2019110412 | 6/2019 |
| WO | 2019229753 | 12/2019 |

OTHER PUBLICATIONS

Balogun. Computer Reviews Journal vol. 2 (2018) ISSN: 2581-6640. http://purkh.com/index.php/tocamp (Year: 2018).*

Toh, Sengwee. Sensitivity and Specificity of Computerized Algorithms to Classify Gestational Periods in the Absence of Information on Date of Conception. American Journal of Epidemiology. vol. 167, No. 6. DOI: 10.1093/aje/kwm367. Jan. 14, 2008. (Year: 2008).*

Title: A Brief Tool to Assess Image-Based Dietary Records and Guide Nutrition Counselling Among Pregnant Women: An Evaluation; JMIR Mhealth and Uhealth vol. 4 Issue: 4 Article No. e123 Published: Oct.-Dec. 2016; By: Ashman.

Title: Biomarkers of Nutrition and Health: New Tools for New Approaches; Nutrients vol. 11 Issue: 5 Article No. 1092 Published: May 2019; By: Pico, Catalina.

Title: Role of Personalized Nutrition in Chronic-Degenerative Diseases; Nutrients vol. 11 Issue: 8 Article No. 1707 Published: Aug. 2019 DOI: 10.3390/nu11081707; By: Di Renzo, Laura.

* cited by examiner

SYSTEM AND METHOD FOR GENERATING A GESTATIONAL DISORDER NOURISHMENT PROGRAM

CROSS-REFERENCE TO RELATED APPLICATIONS

This application is a continuation of Non-provisional application Ser. No. 17/187,983 filed on Mar. 1, 2021, and entitled "SYSTEM AND METHOD FOR GENERATING A GESTATIONAL DISORDER NOURISHMENT PROGRAM," the entirety of which is incorporated herein by reference.

FIELD OF THE INVENTION

The present invention generally relates to the field of artificial intelligence. In particular, the present invention is directed to a system and method for generating a gestational disorder nourishment program.

BACKGROUND

Current edible suggestion systems do not account for the status of pregnancy. This leads to inefficiency of a poor nutrition plan for the mother and/or fetus. This is further complicated by a lack of uniformity of nutritional plans, which results in poor developmental growth.

SUMMARY OF THE DISCLOSURE

In an aspect, a system for generating a gestational disorder nourishment program is disclosed. The system includes a computing device, wherein the computing device is configured to obtain a maternal marker, wherein the maternal marker comprises an uncertainty indicator, receive a conception datum, classify the conception datum to a gestational progression level, determine a gestational disorder as a function of the maternal marker using one or more disorder machine-learning models, wherein determining the gestational disorder includes obtaining a disorder training set that correlates at least a gestational enumeration and a gestational effect to the gestational disorder, training a disorder machine-learning model of the one or more disorder machine-learning models as a function of the disorder training set, wherein the disorder machine-learning model includes one or more disorder machine-learning processes, determining the gestational disorder as a function of the maternal marker using the trained disorder machine-learning model and updating the disorder machine-learning model to incorporate a new gestational enumeration that is related to a modified gestational effect, calculate a gestational phase as a function of the maternal marker, the gestational progression level and the gestational disorder and generate a nourishment program as a function of the gestational phase and a gestational outcome.

In another aspect, a method for generating a gestational disorder nourishment program is disclosed. The method includes obtaining, using a computing device, a maternal marker, wherein the maternal marker comprises an uncertainty indicator, receiving, using the computing device, a conception datum, classifying, using the computing device, the conception datum to a gestational progression level, determining, using the computing device, a gestational disorder as a function of the maternal marker using one or more disorder machine-learning models, wherein determining the gestational disorder includes obtaining a disorder training set that correlates at least a gestational enumeration and a gestational effect to the gestational disorder, training a disorder machine-learning model of the one or more disorder machine-learning models as a function of the disorder training set, wherein the disorder machine-learning model includes one or more disorder machine-learning processes, determining the gestational disorder as a function of the maternal marker using the trained disorder machine-learning model and updating the disorder machine-learning model to incorporate a new gestational enumeration that is related to a modified gestational effect, calculating, using the computing device, a gestational phase as a function of the maternal marker, the gestational progression level and the gestational disorder and generating, using the computing device, a nourishment program as a function of the gestational phase and a gestational outcome.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a gestational disorder nourishment program. In an embodiment, this disclosure obtains a maternal marker. Aspects of the present disclosure can be used to calculate a gestational phase as a function of the maternal marker by identifying a gestational goal. This is so, at least in part, because this disclosure incorporates a machine-learning model. Aspects of the present disclosure can also be used to determine an edible that relates to the gestational phase. Aspects of the present disclosure allow for generating a nourishment program as a function of the edible. Exemplary embodiments illustrating aspects of the present disclosure are described below in the context of several specific examples.

Figure 1:
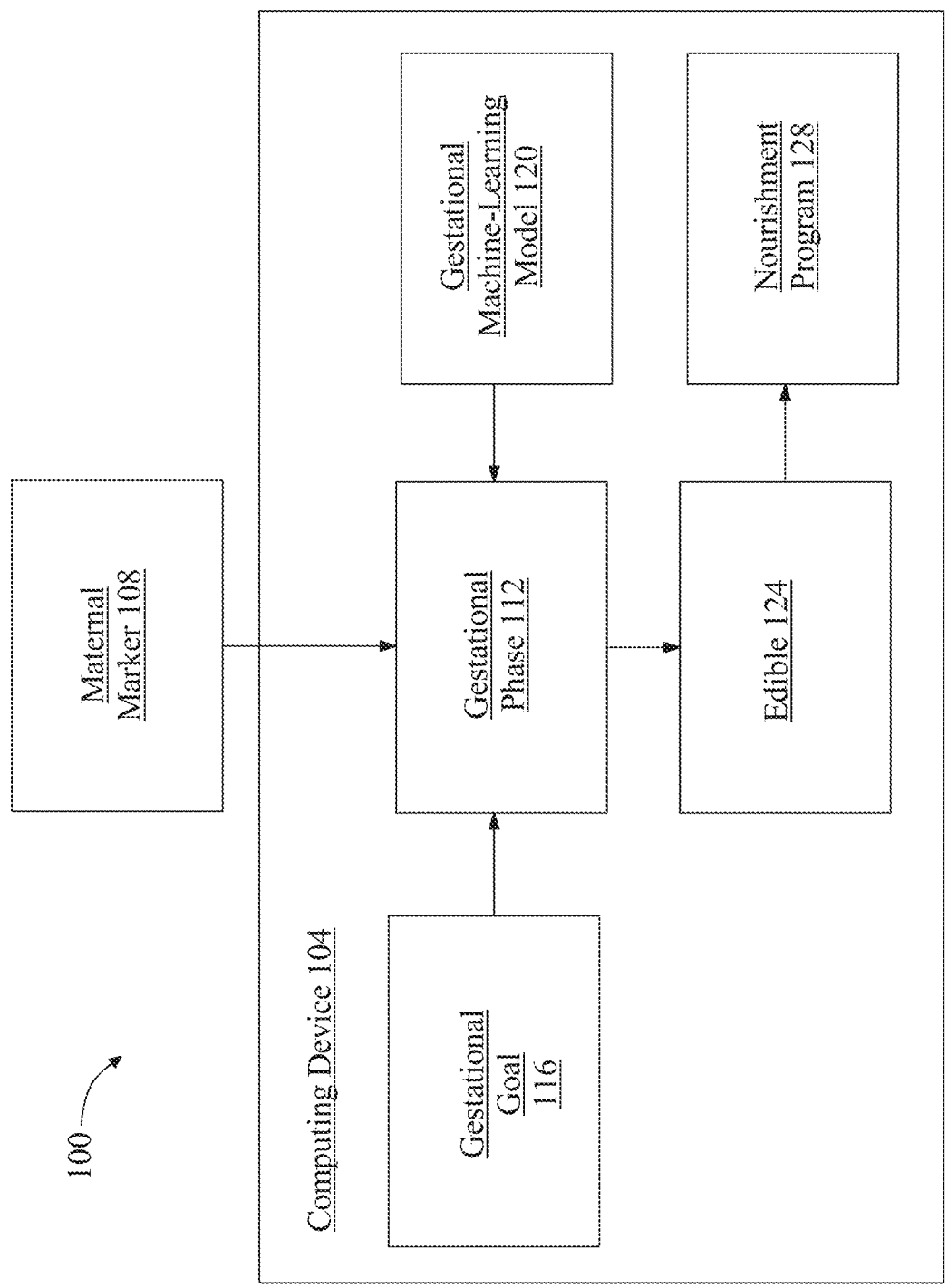
FIG. 1 is a block diagram illustrating an exemplary embodiment of a system for generating a gestational disorder nourishment program.

Referring now to FIG. 1, an exemplary embodiment of a [system 100 for] generating a gestational disorder nourishment program is illustrated. System includes a computing device 104. computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains a maternal marker 108. As used in this disclosure a "maternal marker" is an element of data that denotes a health status of a mother, wherein a health status is a measurement of the relative level of health of a mother. In an embodiment, and without limitation, maternal marker 108 may include a health status of a pregnancy and/or fetal status, wherein a "fetal status", as used herein, is a relative level of health of the fetus developing in the mother's womb. Maternal marker 108 may include a biological sample. As used in this disclosure a "biological sample" is one or more biological specimens collected from a mother and/or fetus. Biological sample may include, without limitation, exhalate, blood, sputum, urine, saliva, feces, semen, amniotic fluid, and other bodily fluids, as well as tissue. Maternal marker 108 may include data collected from a biological sampling device. Maternal marker 108 may include one or more biomarkers. As used in this disclosure a "biomarker" is a molecule and/or chemical that identifies the health status of a mother, pregnancy, and/or fetus. As a non-limiting example, biomarkers may include, human chorionic gonadotrophin, progesterone, creatine kinase, adrenomedullin, pregnancy-associated plasma protein, pregnancy specific beta-glycoprotein I, human placental lactogen, activin A, A-disintegrin, soluble vascular endothelial growth factor receptor 1, placental growth factor, metalloprotease-12, estradiol, inhibin A, interleukin-6, interleukin-8, interleukin-2, tumor necrosis factor alpha, high sensitivity C-reactive protein, leukemia inhibitory factor, glycodelin, vascular endothelial growth factor, and the like thereof. As a further non-limiting example, maternal marker 108 may include datum from one or more devices that collect, store, and/or calculate one or more lights, voltages, currents, sounds, chemicals, pressures, and the like thereof that may be capable of monitoring an infant's health status. As a non-limiting example, maternal marker 108 may be obtained as a function of an ultrasound imaging device such as a doppler ultrasound transducer. As a further non-limiting example maternal marker 108 may be obtained as a function of a nuchal translucency scanning device. Maternal marker 108 may be received as a function of an organ system. As used in this disclosure an "organ system" is a group of organs and/or tissues that work together as a biological system. For example, and without limitation, an organ system may include one or more respiratory systems, digestive systems, excretory systems, circulatory systems, urinary systems, integumentary systems, skeletal systems, muscular systems, endocrine systems, lymphatic systems, nervous systems, reproductive systems, and the like thereof.

Still referring to FIG. 1, computing device 104 may obtain maternal marker 108 by receiving an input from a user. As used in this disclosure "input" is an element of datum that is obtained as a function of a/an informed advisor, medical advisor, physician, nurse, family member, third-party and the like thereof. As used in this disclosure "informed advisor" is an individual that is skilled in a particular area relating to the study of the organ system of individuals. As a non-limiting example input may include a nurse entering input that the mother is experiencing persistent nausea and/or vomiting. As a further non-limiting example, input may include a physician entering input that the mother is experiencing depressive symptoms and/or signs of depression. As a further non-limiting example, inputs may include one or more inputs associated with decreased level of consciousness, abnormal movements of the fetus, decreasing appetite, changes in body temperature, and the like thereof. Input may include one or more inputs from a function of a medical assessment, wherein a "medical assessment" is an evaluation and/or estimation of the health status of a mother and/or fetus. As a non-limiting example medical assessment may include a/an ultrasound for fetal nuchal translucency, ultrasound for fetal nasal bone determination, maternal serum tests, AFP screening tests, abdominal ultrasound, transvaginal ultrasound, amniocentesis, chorionic villus sampling, glucose testing, Group B strep culture testing, and the like thereof. In an embodiment, and without limitation, maternal marker 108 may describe a finding from an ultrasound scan such as a date that a baby's heartbeat is heard or a date when there is first fetal movement. In yet another embodiment, maternal marker 108 may describe one or more measurements obtained from an ultrasound such as a fundal height measurement or a uterus size measurement. Additionally or alternatively, maternal marker 108 may describe a user's due date which may be calculated by an informed advisor, wherein an informed advisor is described above in detail. For example, a physician may calculate a user's due date by adding 280 days to the first day of the user's last menstrual period. Maternal marker 108 may describe a user's conception date which may indicate a possible range of days during which a user's fetus was conceived whether using artificial or natural methods. For example, a date of conception may reflect a range of days during which sexual intercourse may have led to conception. In yet another non-limiting example, a date of conception may reflect a date of an egg retrieval, a date of an embryo transfer, and/or a date of a blastocyst transfer if a fetus is conceived using artificial methods such as in vitro fertilization. Maternal marker 108 may additionally or alternatively include any maternal marker used as a maternal marker as described in U.S. Nonprovisional application Ser. No. 16/778,847, filed on Jan. 31, 2020, and entitled "METHODS AND SYSTEMS FOR PHYSIOLOGICALLY INFORMED GESTATIONAL INQUIRIES," the entirety of which is incorporated herein by reference.

Still referring to FIG. 1, maternal marker 108 may be obtained as a function of identifying one or more uncertainty indicators. As used in this disclosure an "uncertainty indicator" is an indicator that denotes a threat to the health and/or life of the mother and/or fetus. For example, and without limitation uncertainty indicator may include a high-risk pregnancy. Uncertainty indicator may include one or more indicators of existing health conditions that may threaten the health and/or life of the mother and/or fetus. As a non-limiting example, existing health conditions may include high blood pressure, diabetes, HIV, AIDS, anemia, and the like thereof. Uncertainty indicator may include one or more indicators of obesity and/or excessive weight. Uncertainty indicator may include one or more indicators associated with multiple births. As a non-limiting example, multiple births may include twins, triplets, quadruplets, quintuplets, sextuplets, and the like thereof. Uncertainty indicator may include one or more indicators associated with age. As a non-limiting example, pregnancy in teens and/or women over the age of 35 may increase the risk for preeclampsia and/or gestational high blood pressure. Uncertainty indicator may be expressed as a function of an expression of probability. As used in this disclosure an "expression of probability" is a probability associated with a threat to the health and/or life of the mother, fetus, and/or pregnancy. As a non-limiting example, expression of probability may indicate one or more probabilities for the probability of death, probability of a complication, probability of a miscarriage, probability of a birth defect, and the like thereof.

Still referring to FIG. 1, computing device 104 calculates a gestational phase 112 as a function of maternal marker 108. As used in this disclosure a "gestational phase," is any data describing a pregnancy stage, wherein a pregnancy stage may be marked by one or more characteristics of a female as the female carries a developing fetus. In an embodiment, and without limitation, computing device 104 may calculate a gestational phase of the fetus being 24 weeks progressed, wherein the mother thinks the fetus is 32 weeks progressed. In yet another embodiment, computing device 104 may calculate that the development of the fetus is slightly altered and/or modified at week 24, wherein the gestational phase is calculated to be 18 weeks for the fetus rather than the expected 24 weeks. Gestational phase 112 may include a preconception gestation phase where a female may be considering becoming pregnant but is not currently pregnant. During preconception gestational phase a female may aim to identify and modify one or more biomedical, behavioral, and/or social risks to the female's health or pregnancy outcome through prevention and management. For example, during preconception gestational phase a female may start to consume pre-natal vitamins to increase iron stores within her body. In yet another non-limiting example, during preconception gestational phase a female may gradually reduce and/or eliminate consumption of caffeine. Gestational phase 112 may include a conception and implantation phase during which an egg meets up with a sperm cell and fertilization occurs. During a conception and implantation phase a fertilized egg moves to the lining of the uterus and implants to the uterine wall. In an embodiment, a conception and implantation phase may last anywhere from three to seven days. Gestational phase 112 may include a first trimester phase, second trimester phase, and/or third trimester phase as described in detail below, in reference to FIG. 2. Gestational phase 112 may include a postpartum phase which may begin immediately after the birth of a child and last up to two years following the birth of the child. During the postpartum phase a female may nurse her child.

Still referring to FIG. 1, computing device 104 calculates gestational phase 112 as a function of identifying a gestational goal 116. As used in this disclosure a "gestational goal" is a milestone and/or objective for a fetus to develop. For example, and without limitation, a gestational goal may include a fetus to develop organs by week 10 after conception. As a further non-limiting example, gestational goal 116 may include a fetus to have a beating heart by week 5 after conception. As a further non-limiting example, gestational goal 116 may include the fetus to begin producing urine by week 14 after conception. As a further non-limiting example, gestational goal 116 may include a fetus to achieve a weight of 7.5 pounds by week 39 after conception. As a further non-limiting example, gestational goal 116 may include a fetus to achieve a length of 20 inches by week 39 after conception.

Still referring to FIG. 1, computing device 104 calculates gestational phase 112 as a function of maternal marker 108 and gestational goal 116 as a function of a gestational machine-learning model 120. As used in this disclosure "gestational machine-learning model" is a machine-learning model to produce a gestational phase output given maternal markers and gestational goals as inputs; this is in contrast to a non-machine learning software program where the commands to be executed are determined in advance by a user and written in a programming language. Gestational machine-learning model 120 may include one or more gestational machine-learning processes such as supervised, unsupervised, or reinforcement machine-learning processes that computing device 104 and/or a remote device may or may not use in the determination of gestational phase 112. As used in this disclosure "remote device" is an external device to computing device 104. An gestational machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train gestational machine-learning process as a function of a gestational training set. As used in this disclosure "gestational training set" is a training set that correlates a maternal marker and/or gestational goal to a gestational phase. For example, and without limitation, a maternal marker of IL-12 and a gestational goal of a reduced blood pressure may relate to a gestational phase of a first trimester. Gestational training set may be received as a function of user-entered valuations of maternal markers, gestational goals, and/or gestational phases. Computing device 104 may receive gestational training set by receiving correlations of maternal markers, and/or gestational goals that were previously received and/or determined during a previous iteration of determining gestational phases. Gestational training set may be received by one or more remote devices that at least correlate a maternal marker and/or gestational goal to a gestational phase, wherein a remote device is an external device to computing device 104, as described above. Gestational training set may be received in the form of one or more user-entered correlations of a maternal marker and/or gestational goal to a gestational phase. A user may include an informed advisor, wherein an informed advisor may include, without limitation, obstetricians, gynecologists, family physicians, certified nurse-midwife, direct-entry midwife, and the like thereof.

Still referring to FIG. 1, computing device 104 may receive gestational machine-learning model from a remote device that utilizes one or more gestational machine learning processes, wherein a remote device is described above in detail. For example, and without limitation, a remote device may include a computing device, external device, processor, and the like thereof. Remote device may perform the gestational machine-learning process using the gestational training set to generate gestational phase 112 and transmit the output to computing device 104. Remote device may transmit a signal, bit, datum, or parameter to computing device 104 that at least relates to gestational phase 112. Additionally or alternatively, the remote device may provide an updated machine-learning model. For example, and without limitation, an updated machine-learning model may be comprised of a firmware update, a software update, a gestational machine-learning process correction, and the like thereof. As a non-limiting example a software update may incorporate a new maternal marker that relates to a modified gestational goal. Additionally or alternatively, the updated machine learning model may be transmitted to the remote device, wherein the remote device may replace the gestational machine-learning model with the updated machine-learning model and determine the gestational phase as a function of the maternal marker using the updated machine-learning model. The updated machine-learning model may be transmitted by the remote device and received by computing device 104 as a software update, firmware update, or corrected gestational machine-learning model. For example, and without limitation gestational machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

In an embodiment and without limitation, gestational machine-learning model 120 may include a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)±P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

In an embodiment and still referring to FIG. 1, computing device 104 may determine that maternal marker 108 is not suitable for a first gestational phase. As used in this disclosure a "first gestational phase" is a gestational phase associated with a particular stage of pregnancy. First gestational phase may include, without limitation, conception phase, first trimester, second trimester, third trimester, postpartum phase, and the like thereof. Computing device 104 may determine that maternal marker 108 is suitable for a second gestational phase, wherein the second gestational phase occurs after first gestational phase. As used in this disclosure a "second gestational phase" is a gestational phase associated with a particular stage of pregnancy that occurs after first gestational phase. In an embodiment and without limitation, maternal marker 108 may include IL-1-beta during a first gestational phase including a first trimester, wherein computing device 104 may determine that IL-1-beta is not suitable as a maternal marker for the first trimester, rather IL-1-beta is suitable for a second trimester. Computing device 104 may calculate gestational phase by determining a gestational divergence. As used in this disclosure a "gestational divergence" is a quantitative value comprising the magnitude of divergence of maternal marker 108 from a gestational recommendation, wherein a gestational recommendation is a medical guideline and/or recommendation for the measurement of a gestational phase. As a non-limiting example, gestation recommendation may include a recommendation that 400 to 800 IU of vitamin D is consumed each day. Gestational recommendation may be received from a peer review, an advisor association, a medical website, and the like thereof, described in detail below, in reference to FIG. 4. Gestational divergence may be determined as a function of maternal marker 108, gestational recommendation, and a divergence threshold. As used in this disclosure a "divergence threshold" is a parameter that identifies one or more variance limits of the maternal marker from the gestational recommendation. As a non-limiting example, divergence threshold may determine that a maternal marker should not exceed 1.1 mcg/L for the biomarker VEGF. As a further non-limiting, divergence threshold may determine that maternal marker 108 should not exceed 22 for omega-3-fatty acid.

Still referring to FIG. 1, computing device may calculate gestational phase by receiving a conception datum. A "conception datum," as used in this disclosure, is any data that is utilized to calculate a date of conception. Conception datum may describe a fetus's conception date which may be calculated by an informed advisor, wherein an informed advisor is described in detail above. For example, a physician may calculate a fetus's conception date by analyzing a blood analysis from a mother. Conception datum may describe a possible range of days during which a user's baby was conceived whether using artificial or natural methods. For example, a date of conception may reflect a range of days during which sexual intercourse may have led to conception. Computing device 104 may be configured to classify a conception datum to a gestational progression level. As used in this disclosure a "gestational progression level" is a level at which the fetus should be at in relation to the conception datum. For example, and without limitation, conception datum may be received that identifies conception datum may be associated with a fetus being 2 months old, wherein the gestational progression level identifies that the development of the fetus is only at 1 month. As a further non-limiting example, conception datum may be received that identifies a fetus is 34 weeks old, wherein the gestational progression level identifies that the development of the infant is 22 weeks old.

Still referring to FIG. 1, computing device 104 may classify conception datum to gestational progression level by generating a gestational classification algorithm. A "gestational classification algorithm," as used in this disclosure is any calculation and/or series of calculations that identify to which set of categories or "bins" a new observation or input belongs. Generating gestational classification algorithm may include generating a machine learning model using a classification algorithm. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Computing device 104 may utilize gestational classification model that utilizes conception datum as an input and outputs gestational progression level. Computing device 104 may be configured to calculate gestational phase as a function of the gestational classification model.

Still referring to FIG. 1, computing device 104 may identify gestational phase 112 by determining a gestational disorder. As used in this disclosure an "gestational disorder" is an ailment and/or collection of ailments that impact a pregnancy, mother, and/or fetus. As a non-limiting example, gestational disorder may include anemia, depression, ectopic pregnancy, gestational diabetes, preeclampsia, hyperemesis gravidarum, miscarriage, placenta previa, placental abruption, UTI, peripartum cardiomyopathy, cervical insufficiency, amniotic fluid complications, premature labor, venous thrombosis, molar pregnancy, fetal alcohol syndrome, HELLP syndrome, eclampsia, and the like thereof. Gestational disorder may be determined as a function of one or more disorder machine-learning models. As used in this disclosure, a "disorder machine-learning model" is a machine-learning model to produce a gestational disorder output given maternal marker 108 as inputs; this is in contrast to a non-machine learning software program where the commands to be executed are determined in advance by a user and written in a programming language. Disorder machine-learning model may include one or more disorder machine-learning processes such as supervised, unsupervised, or reinforcement machine-learning processes that computing device 104 and/or a remote device may or may not use in the determination of gestational disorder. A disorder machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train disorder machine-learning process as a function of a disorder training set. As used in this disclosure, a "disorder training set" is a training set that correlates at least a gestational enumeration and a gestational effect to a gestational disorder. As used in this disclosure, an "gestational enumeration" is a measurable value associated with the gestational goal. As used in this disclosure, a "gestational effect" is an impact and/or effect the maternal marker has on the pregnancy, mother, and/or fetus. As a non-limiting example, a gestational enumeration of 23 may be related to a gestational effect of a thinning fetal membrane wherein a gestational disorder of ruptures fetal membrane may be determined. The disorder training set may be received as a function of user-entered valuations of gestational enumerations, gestational effects, and/or gestational disorders. Computing device 104 may receive disorder training set by receiving correlations of gestational enumerations and/or gestational effects that were previously received and/or determined during a previous iteration of determining gestational disorders. The disorder training set may be received by one or more remote devices that at least correlate a gestational enumeration and/or gestational effect to a gestational disorder, wherein a remote device is an external device to computing device 104, as described above. The disorder training set may be received in the form of one or more user-entered correlations of a gestational enumeration and gestational effect to a gestational disorder. Additionally or alternatively, a user may include an informed advisor, wherein an informed advisor may include, without limitation, obstetricians, gynecologists, family physicians, certified nurse-midwife, direct-entry midwife, and the like thereof.

Still referring to FIG. 1, computing device 104 may receive disorder machine-learning model from the remote device that utilizes one or more disorder machine learning processes, wherein a remote device is described above in detail. For example, and without limitation, a remote device may include a computing device, external device, processor, and the like thereof. The remote device may perform the disorder machine-learning process using the disorder training set to generate gestational disorder and transmit the output to computing device 104. The remote device may transmit a signal, bit, datum, or parameter to computing device 104 that at least relates to gestational disorders. Additionally or alternatively, the remote device may provide an updated machine-learning model. For example, and without limitation, an updated machine-learning model may be comprised of a firmware update, a software update, a disorder machine-learning process correction, and the like thereof. As a non-limiting example a software update may incorporate a new gestational enumeration that relates to a modified gestational effect. Additionally or alternatively, the updated machine learning model may be transmitted to the remote device, wherein the remote device may replace the disorder machine-learning model with the updated machine-learning model and determine the gestational disorder as a function of the gestational enumeration using the updated machine-learning model. The updated machine-learning model may be transmitted by the remote device and received by computing device 104 as a software update, firmware update, or corrected disorder machine-learning model. For example, and without limitation disorder machine-learning model may utilize a Naïve bayes machine-learning process, wherein the updated machine-learning model may incorporate decision tree machine-learning process.

Still referring to FIG. 1, computing device 104 determines an edible 124 as a function of gestational phase 112. As used in this disclosure an "edible" is a source of nourishment that may be provided to a mother such that the mother may absorb the nutrients from the source. Edible 124 may or may not aid in providing nourishment to the fetus as a function of the mother consuming edible 124. For example and without limitation, an edible may include seafood, vegetables, grains, nuts, dairy, meat, fruit, eggs, honey, insects, poultry, cheese, beans, and the like thereof. Computing device 104 may determine edible 124 as a function of receiving a nourishment composition. As used in this disclosure a "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an "edible directory" is a database of edibles that may be identified as a function of one or more maternal markers, as described in detail below, in reference to FIG. 3.

Still referring to FIG. 1, computing device 104 may produce a nourishment demand as a function of gestational phase 112. As used in this disclosure a "nourishment demand" is requirement and/or necessary amount of nutrients required for a mother to receive. As a non-limiting example, nourishment demand may include a mother requirement of 400 mcg of folic acid, 400 IU of vitamin D, 300 mg of calcium, 70 mg of vitamin C, 3 mg of thiamine, 2 mg of riboflavin, 20 mg of niacin, 6 mcg of vitamin B12, 10 mg of vitamin E, 15 mg of zinc, 17 mg of iron, and/or 150 mcg of iodine to be consumed per day. Nourishment demand may be determined as a function of receiving a nourishment goal. As used in this disclosure a "nourishment goal" is a recommended amount of nutrients that a mother should consume. Nourishment goal may be identified by one or more organizations that relate to, represent, and/or study pregnancy conditions, such as the American Medical Association, American Pregnancy Association, Women's Health, Society for Maternal Fetal Medicine, The American College of Obstetricians and Gynecologists, and the like thereof.

Still referring to FIG. 1, computing device 104 may determine edible 124 as a function of nourishment composition, nourishment demand, and an edible machine-learning model. As used in this disclosure a "edible machine-learning model" is a machine-learning model to produce an edible output given nourishment compositions and nourishment demands as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in the determination of edible 124, wherein a remote device is an external device to computing device 104 as described above in detail. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure an "edible training set" is a training set that correlates at least nourishment composition and nourishment demand to an edible. For example, and without limitation, nourishment composition of 2.4 mg of thiamine and a nourishment demand of 2 mg of thiamine as a function of Wernicke's encephalopathy may relate to an edible of lean pork chops. The edible training set may be received as a function of user-entered valuations of nourishment compositions, nourishment demands, and/or edibles. Computing device 104 may receive edible training set by receiving correlations of nourishment compositions and/or nourishment demands that were previously received and/or determined during a previous iteration of determining edibles. The edible training set may be received by one or more remote devices that at least correlate a nourishment composition and nourishment demand to an edible, wherein a remote device is an external device to computing device 104, as described above. Edible training set may be received in the form of one or more user-entered correlations of a nourishment composition and/or nourishment demand to an edible. Additionally or alternatively, a user may include an informed advisor, wherein an informed advisor may include, without limitation, dermatologists, functional medicine practitioners, chemical pathologists, family physicians, family physicians, and the like thereof. Additionally or alternatively, edible machine-learning model may identify edible 124 as a function of one or more classifiers, wherein classifiers are described above in detail.

Still referring to FIG. 1, computing device 104 may receive edible machine-learning model from a remote device that utilizes one or more edible machine learning processes, wherein remote device is described above in detail. For example, and without limitation, remote device may include a computing device, external device, processor, and the like thereof. Remote device may perform the edible machine-learning process using the edible training set to generate edible 124 and transmit the output to computing device 104. Remote device may transmit a signal, bit, datum, or parameter to computing device 104 that at least relates to edible 124. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment demand. Additionally or alternatively, the updated machine learning model may be transmitted to the remote device, wherein the remote device may replace the edible machine-learning model with the updated machine-learning model and determine the edible as a function of the nourishment demand using the updated machine-learning model. The updated machine-learning model may be transmitted by the remote device and received by computing device 104 as a software update, firmware update, or corrected edible machine-learning model. For example, and without limitation an edible machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 generates a nourishment program 128 as a function of edible 124. As used in this disclosure a "nourishment program" is a program consisting of one or more edibles that are to be administered to a mother over a given time period, wherein a time period is a temporal measurement such as seconds, minutes, hours, days, weeks, months, years, and the like thereof. As a non-limiting example, nourishment program may generate a first nourishment program for a mother that thinks the fetus is 28 weeks progressed, wherein a second nourishment program for the mother may be generated due to the modified development of the fetus that is only 22 weeks progressed. As a further non-limiting example, nourishment program may generate a first nourishment program for a mother that thinks the fetus is 34 weeks progressed, wherein a second nourishment program for the mother may be generated due to the fetus being 29 weeks progressed. As a non-limiting example nourishment program 128 may consist of recommending a mother consume Greek yogurt for 7 days. As a further non-limiting example nourishment program 128 may recommend chickpeas for a first day, sweet potatoes for a second day, and salmon for a third day. In an embodiment, nourishment program 128 may include one or more recommendations of edibles for a mother to consume to alter and/or enhance nourishment compositions of breast milk. As a non-limiting example nourishment program may include one or more recommendations of edibles for a mother to consume, such as recommending salmon to enhance vitamin D concentrations for the developing fetus to receive. As a further non-limiting example, nourishment program 128 may recommend one or more diet programs such as paleo, keto, vegan, vegetarian, and the like thereof.

In an embodiment, and still referring to FIG. 1, computing device 104 may develop nourishment program 128 as a function of a gestational outcome. As used in this disclosure a "gestational outcome" is an outcome that an edible may generate according to a predicted and/or purposeful plan. As a non-limiting example, gestational outcome may include a treatment outcome. As used in this disclosure a "treatment outcome" is an intended outcome that is designed to at least reverse and/or eliminate maternal marker 108 associated with gestational phase 112 and/or gestational disorder. As a non-limiting example, a treatment outcome may include reversing the effects of the gestational disorder preeclampsia. As a further non-limiting example, a treatment outcome includes reversing the gestational disorder of anemia. Gestational outcome may include a prevention outcome. As used in this disclosure a "prevention outcome" is an intended outcome that is designed to at least prevent and/or avert maternal marker 108 associated with gestational phase 112 and/or gestational disorder. As a non-limiting example, a prevention outcome may include preventing the development of the gestational disorder of gestational diabetes.

Still referring to FIG. 1, computing device 104 may develop nourishment program 128 as a function of edible 124 and treatment outcome using a nourishment machine-learning model. As used in this disclosure a "nourishment machine-learning model" is a machine-learning model to produce a nourishment program output given edibles and/or gestational outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the development of nourishment program 128. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a gestational outcome to an edible. The nourishment training set may be received as a function of user-entered edibles, gestational outcomes, and/or nourishment programs. For example, and without limitation, a gestational outcome of treating gestational anemia may correlate to an edible of iron. Computing device 104 may receive nourishment training by receiving correlations of gestational outcomes and/or edibles that were previously received and/or determined during a previous iteration of developing nourishment programs. The nourishment training set may be received by one or more remote devices that at least correlate a gestational outcome and/or edible to a nourishment program, wherein a remote device is an external device to computing device 104, as described above. Nourishment training set may be received in the form of one or more user-entered correlations of a gestational outcome and/or edible to a nourishment program. Additionally or alternatively, a user may include an informed advisor, wherein an informed advisor may include, without limitation, obstetricians, gynecologists, family physicians, certified nurse-midwife, direct-entry midwife, and the like thereof.

Still referring to FIG. 1, computing device 104 may receive nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to develop nourishment program 128 and transmit the output to computing device 104. The remote device may transmit a signal, bit, datum, or parameter to computing device 104 that at least relates to nourishment program 128. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new gestational outcome that relates to a modified edible. Additionally or alternatively, the updated machine learning model may be transmitted to the remote device, wherein the remote device may replace the nourishment machine-learning model with the updated machine-learning model and develop the nourishment program as a function of the gestational outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a neural net machine-learning process, wherein the updated machine-learning model may incorporate decision tree machine-learning processes.

Figure 2:
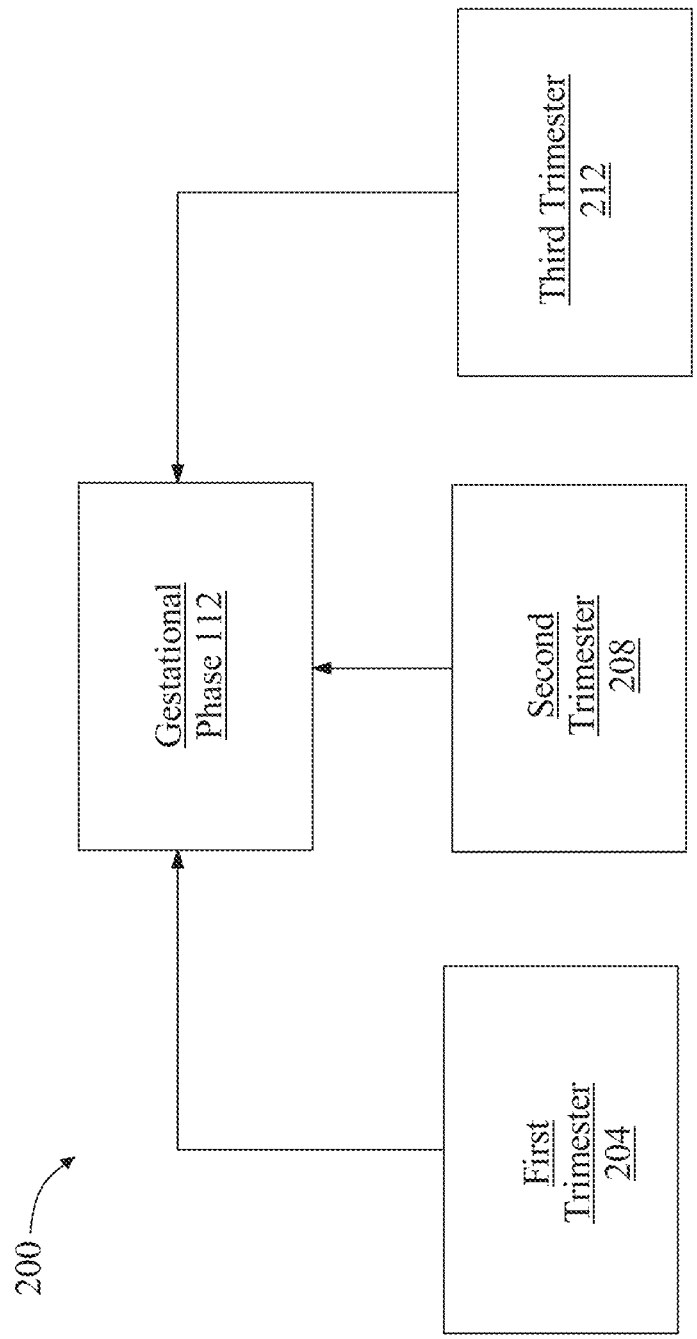
FIG. 2 is a block diagram of an exemplary embodiment of a gestational phase according to an embodiment of the invention.

Now referring to FIG. 2, an exemplary embodiment 200 of a gestational phase 112 is illustrated. Gestational phase 112 may include a first trimester 204. As used in this disclosure a "first trimester" is the time period that starts at the date of conception and ends at week 12 of the pregnancy. First trimester 204 may include the time period in which the embryo implants itself into the uterine wall. First trimester 204 may include the growth and development of an amniotic sac. As used in this disclosure an "amniotic sac" is a sac filled with amniotic fluid and surrounds the fetus. For example and without limitation amniotic sac may protect the fetus from injury and/or regulate the temperature of the fetus. First trimester 204 may include the growth and development of a placenta. As used in this disclosure a "placenta" is a flat shaped organ that exchanges nourishment and/or waste products. Placenta may attach to the uterine wall with villi, wherein villi are tiny projections of tissue. Placenta may exchange nourishment and/or waste products with the mother's blood, wherein the mother's blood and the fetal blood exchange nourishment and/or waste products across a thin membrane. First trimester 204 may include an umbilical cord. As used in this disclosure an "umbilical cord" is a rope-like cord connecting the fetus to the placenta. For example, and without limitation, umbilical cord may contain two arteries and/or a vein that may carry oxygen and/or nutrients to the fetus and/or waste products away from the fetus. In an embodiment and without limitation, first trimester 204 may include an enlargement of the mammary glands of the mother due to increased amount of the hormones estrogen, progesterone, and the like thereof. In yet another embodiment and without limitation, first trimester 204 may include an enlargement of the breasts and/or waist of the mother to accommodate the growing fetus.

Still referring to FIG. 2, gestational phase 112 may include a second trimester 208. As used in this disclosure a "second trimester" is the time period that starts at 12 weeks after the date of conception and ends at 24 weeks after the date of conception. Second trimester 208 may include the time point where all of the organs and systems of the fetus have developed and will start increasing in size and weight. Second trimester 208 may include a time period wherein the umbilical cord thickens allowing more nourishment to be carried to the fetus. In an embodiment, the thickening of the umbilical cord may also allow harmful substances such as alcohol, nicotine, and other illicit drugs to pass through the now thickened umbilical cord. Second trimester 208 may include a period of time wherein the mother's appetite increases. Second trimester 208 may include a time period wherein the fetus may shift, move, and/or budge in the uterus such that the mother and/or other individuals may feel and/or notice the movement. Second trimester 208 may include a period of time wherein the uterus has grown to the height of the belly button of the mother, making the pregnancy visible to other individuals.

Still referring to FIG. 1, gestational phase 112 may include a third trimester 212. As used in this disclosure a "third trimester" is the time period that starts at 24 weeks after the date of conception and ends at 40 weeks after the date of conception. Third trimester 212 may include a time period wherein the fetus continues to grow in weight and/or size. Third trimester 212 may include a time period wherein the mother may experience an increase in skin temperature as the fetus radiates body heat. Third trimester 212 may include a time period wherein the mother may experience increased urinary frequency due to pressure being placed on the bladder. Third trimester 212 may include a time period wherein the mother may experience a blood pressure decrease as the fetus presses on the main vein of the mother. Third trimester 212 may include a time period wherein the mother may experience Braxton-Hicks contractions. Third trimester 212 may include a time period wherein the mother may experience colostrum leakage from the nipples of the mother.

Figure 3:
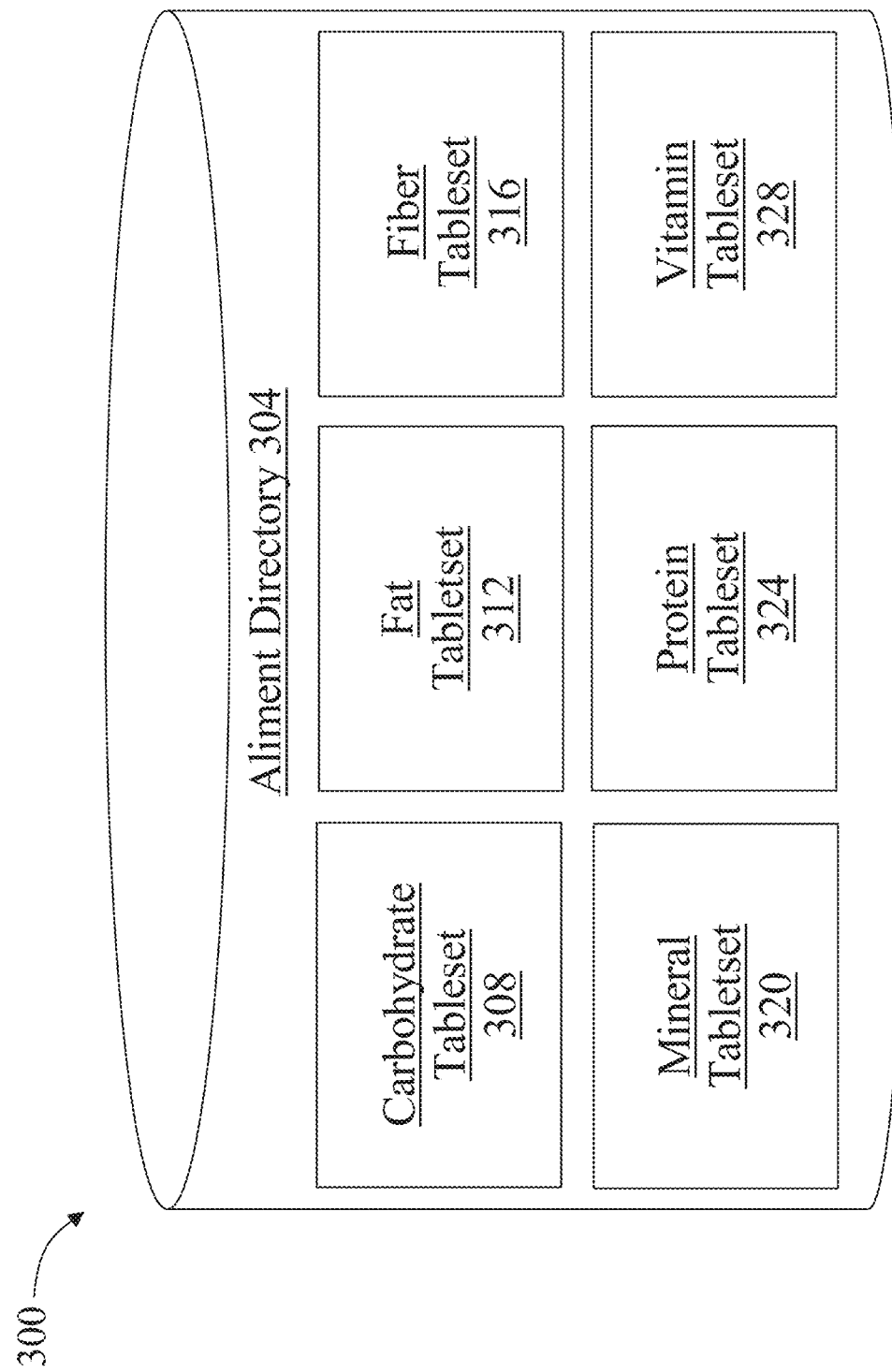
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, psyllium, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorus, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
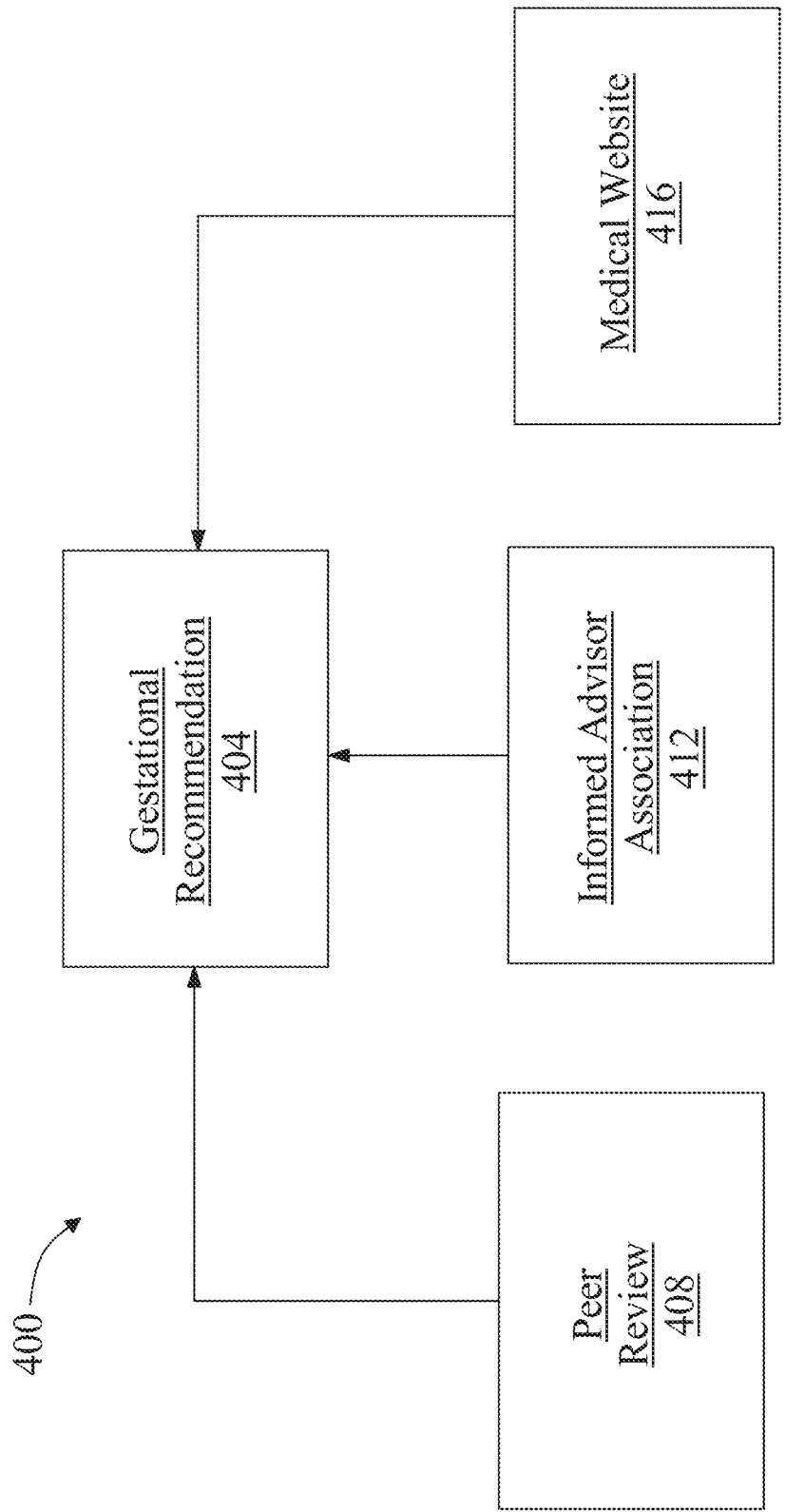
FIG. 4 is a block diagram of an exemplary embodiment of a gestational recommendation according to an embodiment of the invention.

Now referring to FIG. 4, an exemplary embodiment 400 of a gestational recommendation 404 according to an embodiment of the invention is illustrated. As used in this disclosure a "gestational recommendation" is a medical guideline and/or recommendation for the measurement of a gestational phase. As a non-limiting example, gestational recommendation 404 may include a recommendation that a heartbeat of a fetus should develop at 5 weeks after conception. As a further non-limiting example, gestational recommendation 404 may include a recommendation that a fetus should be moving in the womb at 18 weeks. Gestational recommendation 404 may include a peer review 408. As used in this disclosure a "peer review" is a source that establishes a guideline as a function of an evaluation conducted by one or more people with similar competencies. As a non-limiting example peer review 408 may include professional peer reviews, scholarly peer reviews, government peer reviews, medical peer reviews, technical peer reviews, and the like thereof. As a further non-limiting example, peer review 408 may include one or more scholarly journals associated with gestation such as, but not limited to, The Journal of Pregnancy and Childbirth, The Journal of Pregnancy, BMC Pregnancy and Childbirth, Pregnancy Scientific Journals, Journal of Pregnancy and Reproduction, and the like thereof. Gestational recommendation 404 may include an informed advisor association 412. As used in this disclosure an "informed advisor association" is a source of one or more committees, organizations, and/or groups capable of determining and/or organizing recommendations and/or guidelines. As a non-limiting example informed advisor association 412 may include the American Medical Association, American Pregnancy Association, Women's Health, Society for Maternal Fetal Medicine, The American College of Obstetricians and Gynecologists, and the like thereof. Gestational Recommendation 404 may include a medical website 416. As used in this disclosure a "medical website" is a source that establishes a guideline as a function of one or more online and/or web-based medical recommendations for gestation. As a non-limiting example medical website 416 may include AmericanPregnancy, Womenshealth, FDA, Mothertobaby, Whattoexpect, Childbirthconnection, Medline Plus, Drugs.com, Mayo Clinic, Orphanet, Medgadget, WebMD, Health.gov, SPM ePatients blog, and the like thereof. As a further non-limiting example, medical website may include one or more medical blog websites such as, but not limited to, Health, Medicine, Medical Xpress, GeriPal, Chart, Law, Health Policy, MassDevice, Medgadget, Mental health, MomMD LLC, and the like thereof.

Figure 5:
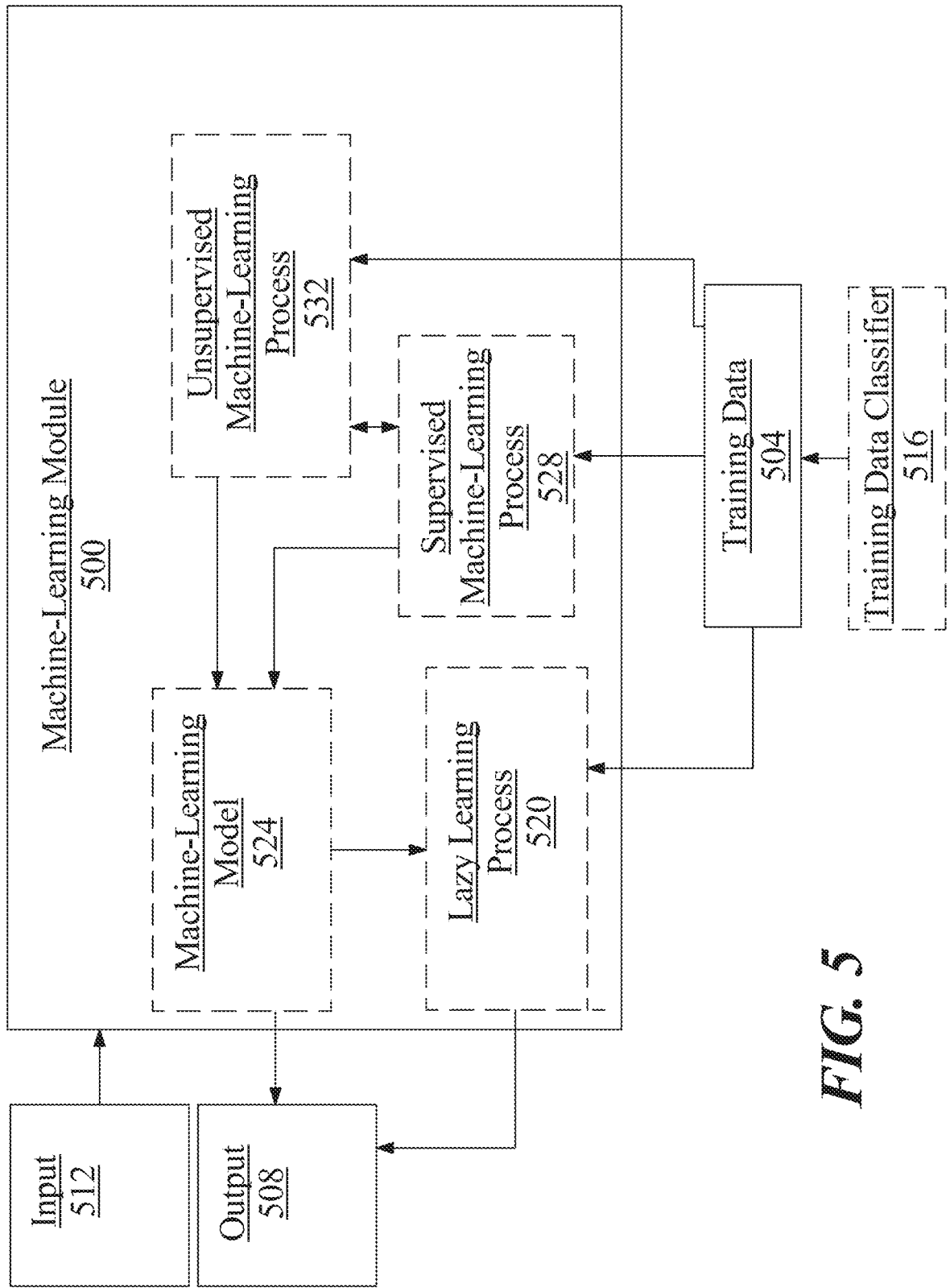
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs such as maternal markers and/or gestational goals may result in an output of a gestational phase.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of gestational goals, such as growth milestones, nourishment goals, developmental goals, and the like thereof.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include maternal markers and/or gestational goals as described above as inputs, gestational phases as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
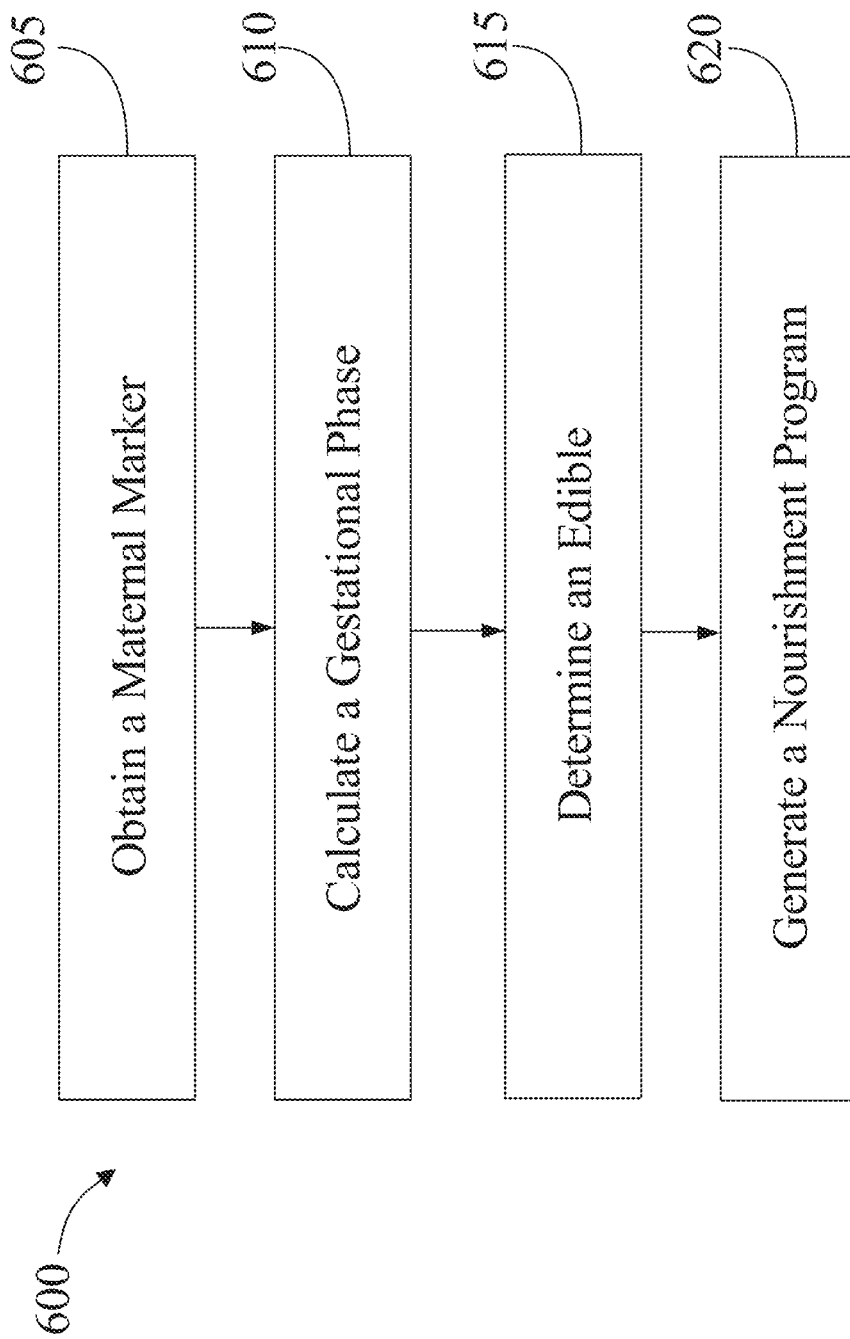
FIG. 6 is a process flow diagram illustrating an exemplary embodiment of a method of generating a gestational disorder nourishment program.

Now referring to FIG. 6, an exemplary embodiment of a method 600 for generating a gestational disorder nourishment program is illustrated. At step 605, a computing device 104 obtains a maternal marker 108. Computing device 104 includes any of the computing device 104 as described above, in reference to FIGS. 1-5. Maternal marker 108 includes any of the maternal marker 108 as described above, in reference to FIGS. 1-5.

Still referring to FIG. 6, at step 610, computing device 104 calculates a gestational phase 112 as a function of maternal marker 108. Gestational phase 112 includes any of the gestational phase 112 as described above, in reference to FIGS. 1-5. Computing device 104 calculates gestational phase 112 by identifying a gestational goal 116. Gestational goal 116 includes any of the gestational goal 116 as described above, in reference to FIGS. 1-5. Computing device 104 calculates gestational phase 112 as a function of maternal marker 108 and gestational goal 116 as a function of a gestational machine-learning model 120. Gestational machine-learning model 120 includes any of the gestational machine-learning model 120 as described above, in reference to FIGS. 1-5.

Still referring to FIG. 6, at step 615, computing device 104 determines an edible 124 as a function of gestational phase 112. Edible 124 includes any of the edible 124 as described above, in reference to FIGS. 1-5.

Still referring to FIG. 6, at step 620, computing device 104 generates a nourishment program 128 as a function of edible 124. Nourishment program 128 includes any of the nourishment program 128 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
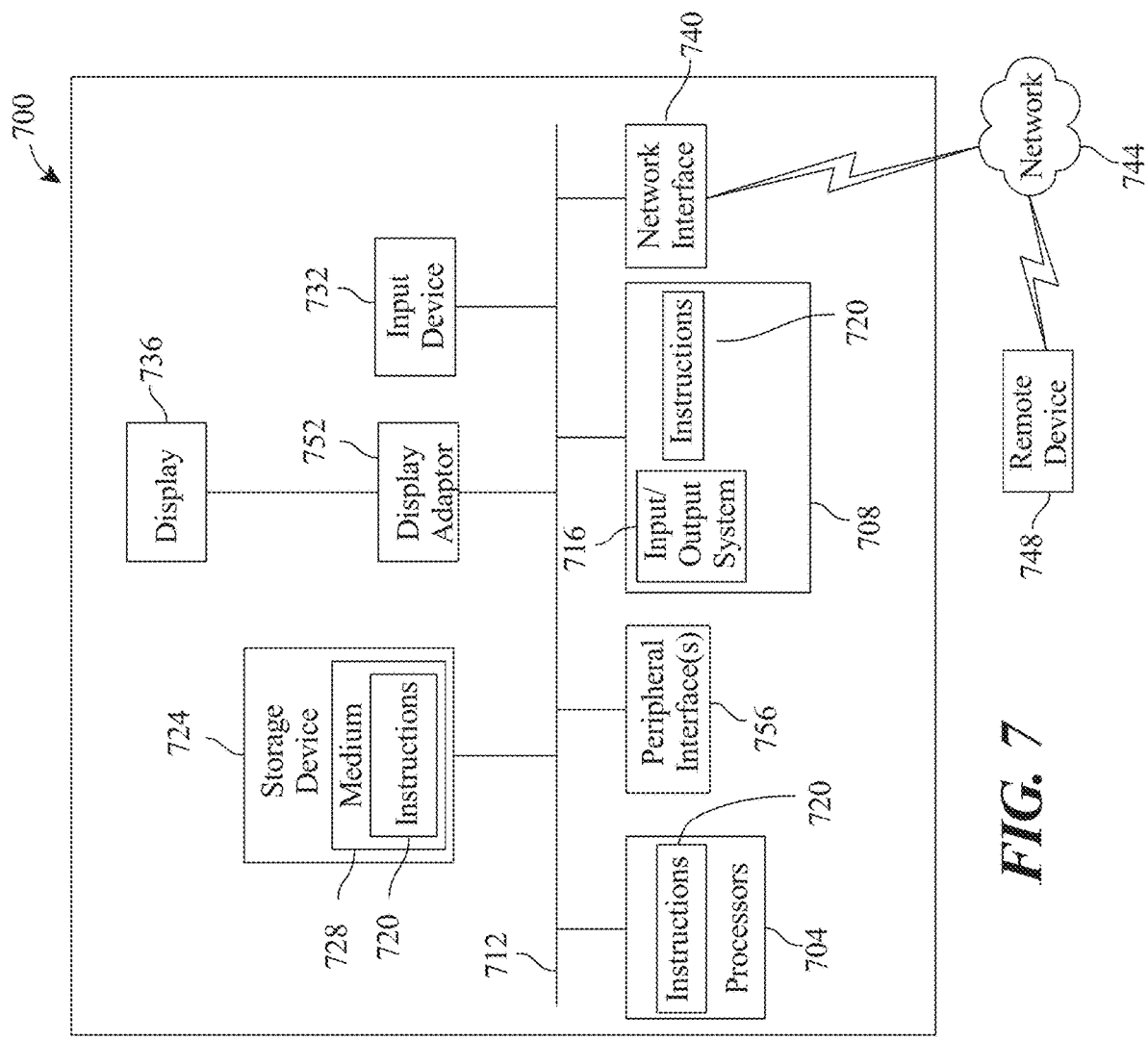
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a gestational disorder nourishment program, the system comprising:
   a computing device, wherein the computing device is configured to:
   obtain a maternal marker, wherein the maternal marker comprises an uncertainty indicator;
   receive a conception datum;
   classify the conception datum to a gestational progression level;
   determine a gestational disorder as a function of the maternal marker using one or more disorder machine-learning models, wherein determining the gestational disorder comprises:
   obtaining a disorder training set that correlates at least a gestational enumeration and a gestational effect to the gestational disorder;
   training a disorder machine-learning model of the one or more disorder machine-learning models as a function of the disorder training set, wherein the disorder machine-learning model comprises one or more disorder machine-learning processes;
   determining the gestational disorder as a function of the maternal marker using the trained disorder machine-learning model; and
   updating the disorder machine-learning model to incorporate a new gestational enumeration that is related to a modified gestational effect;
   calculate a gestational phase as a function of the maternal marker, the gestational progression level, and the gestational disorder, wherein calculating the gestational phase further comprises determining a gestational divergence wherein the gestational divergence indicates a magnitude of divergence of the maternal marker from a gestational recommendation;
   generate a gestational outcome wherein the gestation outcome comprises a treatment outcome, wherein the treatment outcome comprises at least a preventative measure associated with the gestational disorder determined using the trained disorder machine-learning model;
   train a nourishment machine-learning model, wherein training the nourishment machine-learning model comprises:
   receiving a nourishment training set comprising the generated gestational outcome as input correlated to an edible output; and
   training the nourishment machine-learning model using the nourishment training set; and generate a nourishment program as a function of the gestational phase and the trained nourishment machine-learning model.

2. The system of claim 1, wherein the computing device is further configured to receive the maternal marker from an informed advisor, wherein the maternal marker further comprises a medical assessment.

3. The system of claim 1, wherein the conception datum indicates a conception method.

4. The system of claim 1, wherein the computing device is further configured to:
determine that the maternal marker is not suitable for a first gestational phase; and
determine that the maternal marker is suitable for a second gestational phase wherein the second gestational phase occurs after the first gestational phase.

5. The system of claim 1, wherein the computing device is further configured to:
generate a gestational classification model comprising gestational classification algorithm, wherein the gestational classification model utilizes the conception datum as an input and outputs the gestational progression level; and
classify the conception datum to the gestational progression level as a function of the gestational classification model.

6. The system of claim 1, wherein the computing device is further configured to:
determine an edible as a function of the gestational phase; and
generate the nourishment program as a function of the edible.

7. The system of claim 1, wherein the computing device is configured to update the nourishment machine-learning model to incorporate a new gestational outcome related to a modified edible using a remote device.

8. The system of claim 1, wherein the gestational outcome comprises a treatment outcome.

9. The system of claim 1, wherein the gestational outcome comprises a prevention outcome.

10. A method for generating a gestational disorder nourishment program, the method comprising:
obtaining, using a computing device, a maternal marker, wherein the maternal marker comprises an uncertainty indicator;
receiving, using the computing device, a conception datum;
classifying, using the computing device, the conception datum to a gestational progression level;
determining, using the computing device, a gestational disorder as a function of the maternal marker using one or more disorder machine-learning models, wherein determining the gestational disorder comprises:
obtaining a disorder training set that correlates at least a gestational enumeration and a gestational effect to the gestational disorder;
training a disorder machine-learning model of the one or more disorder machine-learning models as a function of the disorder training set, wherein the disorder machine-learning model comprises one or more disorder machine-learning processes;
determining the gestational disorder as a function of the maternal marker using the trained disorder machine-learning model; and
updating the disorder machine-learning model to incorporate a new gestational enumeration that is related to a modified gestational effect;
calculating, using the computing device, a gestational phase as a function of the maternal marker, the gestational progression level and the gestational disorder, wherein calculating the gestational phase further comprises determining a gestational divergence wherein the gestational divergence indicates a magnitude of divergence of the maternal marker from a gestational recommendation;
generating, using the computing device, a gestational outcome wherein the gestation outcome comprises a treatment outcome, wherein the treatment outcome comprises at least a preventative measure associated with the gestational disorder determined using the trained disorder machine-learning model;
training, using the computing device, a nourishment machine-learning model, wherein training the nourishment machine-learning model comprises:
receiving a nourishment training set comprising the generated gestational outcome as input correlated to an edible output; and
training the nourishment machine-learning model using the nourishment training set; and
generating, using the computing device, a nourishment program as a function of the gestational phase and the trained nourishment machine-learning model.

11. The method of claim 10, further comprising:
receiving, using the computing device, the maternal marker from an informed advisor, wherein the maternal marker further comprises a medical assessment.

12. The method of claim 10, wherein the conception datum indicates a conception method.

13. The method of claim 10, further comprising:
determining, using the computing device, that the maternal marker is not suitable for a first gestational phase; and
determining, using the computing device, that the maternal marker is suitable for a second gestational phase wherein the second gestational phase occurs after the first gestational phase.

14. The method of claim 10, further comprising:
generating, using the computing device, a gestational classification model comprising gestational classification algorithm, wherein the gestational classification model utilizes the conception datum as an input and outputs the gestational progression level; and
classifying, using the computing device, the conception datum to the gestational progression level as a function of the gestational classification model.

15. The method of claim 10, further comprising:
determining, using the computing device, an edible as a function of the gestational phase; and
generating, using the computing device, the nourishment program as a function of the edible.

16. The method of claim 10, further comprising:
updating, using the computing device, the nourishment machine-learning model to incorporate a new gestational outcome related to a modified edible using a remote device.

17. The method of claim 10, wherein the gestational outcome comprises a treatment outcome.

18. The method of claim 10, wherein the gestational outcome comprises a prevention outcome.

* * * * *